United States Patent
Isa et al.

(10) Patent No.: US 10,717,447 B2
(45) Date of Patent: Jul. 21, 2020

(54) VISUAL PERCEPTION ASSISTANCE SYSTEM AND VISUAL-PERCEPTION TARGET OBJECT DETECTION SYSTEM

(71) Applicant: MAZDA MOTOR CORPORATION, Hiroshima (JP)

(72) Inventors: Tadashi Isa, Kyoto (JP); Masatoshi Yoshida, Okazaki (JP); Richard Veale, Kyoto (JP); Yusaku Takeda, Hiroshima (JP); Toshihiro Hara, Higashihiroshima (JP); Koji Iwase, Hiroshima (JP); Atsuhide Kishi, Hiroshima (JP); Kazuo Nishikawa, Hiroshima (JP); Takahide Nozawa, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 149 days.

(21) Appl. No.: 16/062,591

(22) PCT Filed: Dec. 16, 2016

(86) PCT No.: PCT/JP2016/087533
§ 371 (c)(1),
(2) Date: Jun. 14, 2018

(87) PCT Pub. No.: WO2017/104794
PCT Pub. Date: Jun. 22, 2017

(65) Prior Publication Data
US 2018/0362053 A1 Dec. 20, 2018

(30) Foreign Application Priority Data

Dec. 17, 2015 (JP) ................................. 2015-246061

(51) Int. Cl.
*G06K 9/00* (2006.01)
*B60W 50/14* (2020.01)
(Continued)

(52) U.S. Cl.
CPC ............... *B60W 50/14* (2013.01); *A61B 5/18* (2013.01); *B60K 35/00* (2013.01); *B60R 1/00* (2013.01);
(Continued)

(58) Field of Classification Search
CPC .... G06F 3/011; G06F 3/0304; G06F 16/2264; G06F 16/9024; G06F 3/0346;
(Continued)

(56) References Cited

U.S. PATENT DOCUMENTS 5,541,590 A * 7/1996 Nishio .................... B60K 28/14
340/903
9,007,197 B2 * 4/2015 Breed ................. G06K 9/00791
340/435

FOREIGN PATENT DOCUMENTS

JP 2003-327009 A 11/2003
JP 2009-237776 A 10/2009
(Continued)

OTHER PUBLICATIONS

International Search Report issued in PCT/JP2016/087533; dated Jan. 17, 2017.

*Primary Examiner* — Duy M Dang
(74) *Attorney, Agent, or Firm* — Studebaker & Brackett PC

(57) ABSTRACT

The present invention includes: a visual perception target determination unit for determining a visual perception target by using a saliency model for determining that an object to be visually perceived at a glance is a visual perception target, a surprise model for determining that an object behaving abnormally is a visual perception target, and a normative model for determining that an object to be visually perceived by a viewing action of a driver serving as a norm is a visual perception target; and a visual guidance unit for determining whether or not an overlooked visual perception to which a (Continued)

line-of-sight direction detected by a line-of-sight detection unit is not directed is present, and guiding a line-of-sight of a driver toward the overlooked visual perception target, when the overlooked visual perception target is present.

10 Claims, 7 Drawing Sheets

(51) Int. Cl.
| | |
|---|---|
| *G02B 27/00* | (2006.01) |
| *B60R 1/00* | (2006.01) |
| *G02B 27/01* | (2006.01) |
| *G08G 1/0962* | (2006.01) |
| *G08G 1/16* | (2006.01) |
| *A61B 5/18* | (2006.01) |
| *B60K 35/00* | (2006.01) |
| *B60Q 9/00* | (2006.01) |

(52) U.S. Cl.
CPC ......... *G02B 27/00* (2013.01); *G02B 27/0093* (2013.01); *G02B 27/01* (2013.01); *G06K 9/00805* (2013.01); *G06K 9/00845* (2013.01); *G08G 1/09623* (2013.01); *G08G 1/166* (2013.01); *B60K 2370/149* (2019.05); *B60K 2370/1529* (2019.05); *B60K 2370/193* (2019.05); *B60K 2370/194* (2019.05); *B60K 2370/21* (2019.05); *B60K 2370/334* (2019.05); *B60Q 9/008* (2013.01); *B60R 2300/205* (2013.01); *B60R 2300/308* (2013.01); *B60W 2050/146* (2013.01); *G02B 2027/014* (2013.01); *G02B 2027/0138* (2013.01); *G02B 2027/0141* (2013.01); *G06K 9/0061* (2013.01)

(58) Field of Classification Search
CPC ...... A63F 13/213; A63F 13/24; A63F 13/426; A63F 13/428; A63F 13/655; A63F 13/00; G06T 7/73; G06K 9/00771; G06K 9/6202; G06K 9/00221; G06K 9/00335; G06K 9/00369; G06K 9/627; G06K 9/00718; G06K 9/6256; G06K 9/62; G06K 2209/21; H04N 7/181; H04N 5/2226; G08C 17/00; G08C 17/02; G06N 3/04; G06N 3/02; G06N 3/08; G08B 13/196; G08B 13/19608; G08B 13/19606; B64C 39/024; B64C 2201/00; G05D 1/0033; G05D 1/0038; G05D 1/0044; G05D 1/0231; G05D 1/0214; G05D 1/0212; A61B 2034/2065; B60T 2210/00; B60T 2210/30; B60T 2210/32; G08G 1/0968; G01C 21/3626
See application file for complete search history.

(56) References Cited

FOREIGN PATENT DOCUMENTS

| | | |
|---|---|---|
| JP | 2010-142410 A | 7/2010 |
| JP | 2012-234410 A | 11/2012 |
| JP | 2014-109958 A | 6/2014 |
| JP | 2014-120111 A | 6/2014 |
| JP | 2015-011457 A | 1/2015 |

* cited by examiner

US 10,717,447 B2

VISUAL PERCEPTION ASSISTANCE SYSTEM AND VISUAL-PERCEPTION TARGET OBJECT DETECTION SYSTEM

TECHNICAL FIELD

The present invention relates to a visual perception assistance system and a visual perception target detection system.

BACKGROUND ART

It is preferable for safety driving to allow a driver to perceive the presence of a hazardous object (obstacle) around the driver, when the driver drives an automobile as an example of a moving body. Patent Literature 1 discloses a technique of detecting a line-of-sight direction of a driver, and displaying a warning indication when the line-of-sight direction of the driver is not directed toward a signal or a road sign ahead of an own vehicle. Further, Patent Literature 2 discloses a technique of guiding a line-of-sight of a driver toward an obstacle ahead of a vehicle, when the obstacle is detected by a camera or the like. Further, Patent Literature 3 discloses a technique of determining an object to be identified by a driver from among objects around an automobile, and determining whether or not a line-of-sight of the driver is directed toward the object to be identified.

It is extremely preferable for safety driving to allow a driver to securely perceive a visual perception target (identifying object) to be visually perceived (identified). However, as a premise, it is necessary to securely grasp a visual perception target that a driver should visually perceive. Further, it is also important to provide measures for allowing a driver to perceive a visual perception target, which may be overlooked by the driver.

CITATION LIST

Patent Literature

Patent Literature 1: Japanese Unexamined Patent Publication No. 2014-120111
Patent Literature 2: Japanese Unexamined Patent Publication No. 2012-234410
Patent Literature 3: Japanese Unexamined Patent Publication No. 2015-11457

SUMMARY OF INVENTION

In view of the above, a first object of the present invention is to provide a visual perception assistance system, which enables to securely detect a visual perception target that a driver should visually perceive, and to securely allow the driver to visually perceive the detected visual perception target.

Further, a second object of the present invention is to provide a visual perception target detection system, which enables to securely detect a visual perception target that an observer should look at.

A visual perception assistance system according to an aspect of the present invention includes:
a surrounding condition acquisition unit for acquiring a surrounding condition of a moving body to be driven by a driver;
a visual perception target determination unit for determining a visual perception target being an object that the driver should look at in a surrounding condition acquired by the surrounding condition acquisition unit;
a line-of-sight direction detection unit for detecting a line-of-sight direction of the driver; and
a visual guidance unit for determining whether or not an overlooked visual perception target to which a line-of-sight direction detected by the line-of-sight direction detection unit is not directed is present among the visual perception target determined by the visual perception target determination unit, and guiding a line-of-sight of the driver toward the overlooked visual perception target, when the overlooked visual perception target is present, wherein
the visual perception target determination unit determines the visual perception target, based on three visual perception models prepared in advance, and
the three visual perception models include a saliency model for determining that an object to be visually perceived at a glance is a visual perception target, a surprise model for determining that an object behaving abnormally is a visual perception target, and a normative model for determining that an object to be visually perceived by a viewing action of a driver serving as a norm is a visual perception target.

Further, a visual perception target detection system according to another aspect of the present invention includes:
a surrounding condition acquisition unit for acquiring a surrounding condition of an observer; and
a visual perception target determination unit for determining a visual perception target being an object that the observer should look at in a surrounding condition acquired by the surrounding condition acquisition unit, wherein
the visual perception target determination unit determines the visual perception target, based on three visual perception models prepared in advance, and
the three visual perception models include a saliency model for determining that an object to be visually perceived at a glance is a visual perception target, a surprise model for determining that an object behaving abnormally is a visual perception target, and a normative model for determining that an object to be visually perceived by a viewing action of an observer serving as a norm is a visual perception target.

According to the aforementioned configuration, it is possible to guide the line-of-sight of the driver to the visual perception target, which may be overlooked by the driver. Further, according to the aforementioned configuration, it is possible to securely detect the visual perception target that the observer should visually perceive.

DESCRIPTION OF EMBODIMENTS

Figure 1:
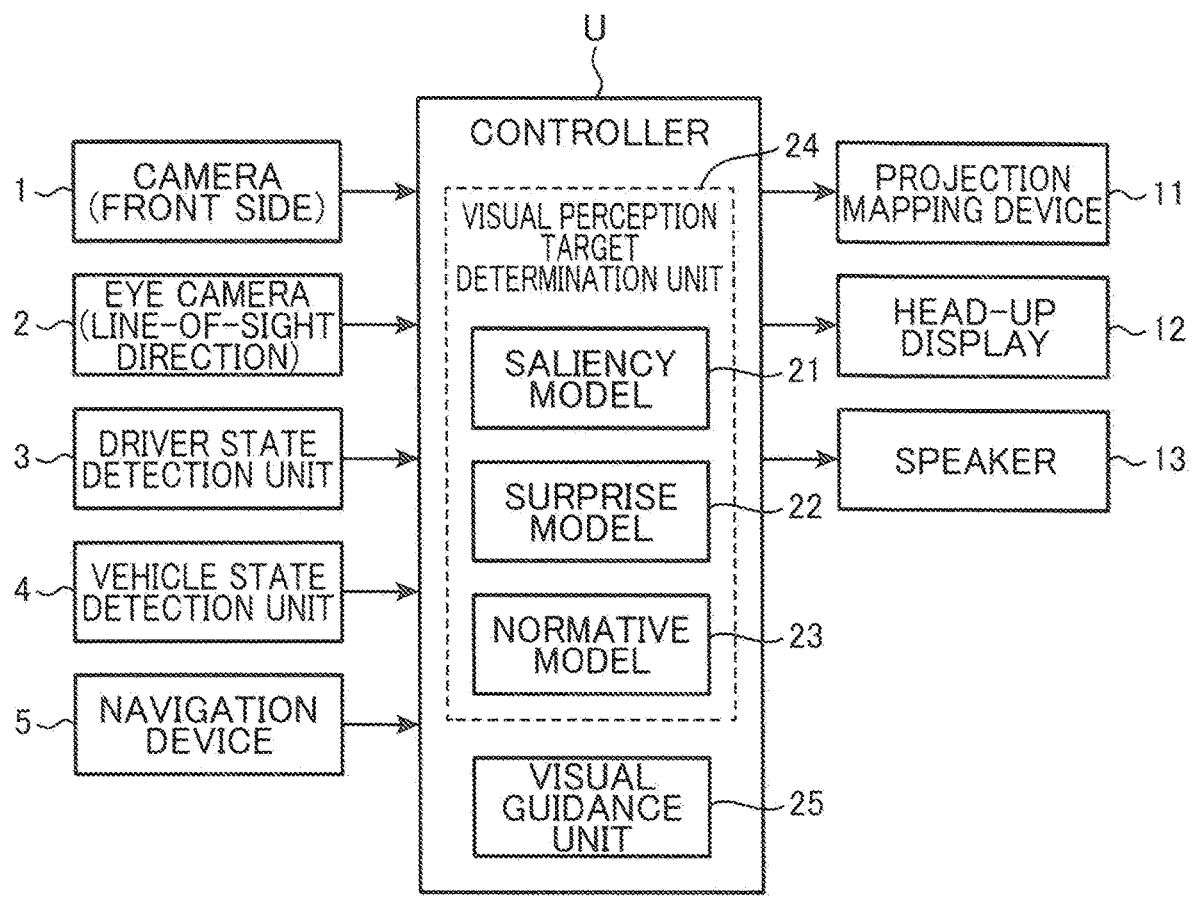
FIG. 1 is a block diagram illustrating an example of a configuration of a control system according to the present invention.

FIG. 1 is a block diagram illustrating an example of a configuration of a visual perception assistance system according to an embodiment of the present invention. The visual perception assistance system is mounted in an automobile (own vehicle) as a moving body. The visual perception assistance system includes a controller U (control unit) constituted by using a microcomputer. Further, the visual perception assistance system includes a camera (an example of a surrounding condition acquisition unit), an eye camera 2 (an example of a line-of-sight direction detection unit), a driver state detection unit 3, a vehicle state detection unit 4, a navigation device 5, a projection mapping device 11, a head-up display 12, and a speaker 13.

The controller U receives signals from device components such as various types of sensors, the camera 1, the eye camera 2, the driver state detection unit 3, the vehicle state detection unit 4, and the navigation device 5.

The camera 1 is a camera for photographing an area ahead of the own vehicle. A surrounding condition ahead of the own vehicle is acquired by the camera 1. The camera 1 is constituted by a color stereo camera, for example. Thus, it is possible to detect a distance from the own vehicle to a visual perception target, and a color of the visual perception target. In this example, a distance to a visual perception target is detected by using the camera 1. The present invention, however, is not limited to the above. A distance to a visual perception target may be detected by using a radar device.

The eye camera 2 is mounted in a vehicle compartment of the own vehicle, and detects a line-of-sight direction of a driver. The eye camera 2 may acquire an image of the driver's eyes, extract a reference point such as a corner of the eye or an inner corner of the eye, and a moving point such as the pupil from the acquired image, and detect a line-of-sight direction within an actual space, based on a position of the moving point with respect to the reference point. The line-of-sight direction is represented by a straight line within a three-dimensional coordinate space in which the own vehicle is set as a reference, for example. In addition to the above, the eye camera 2 also detects a line-of-sight state of the driver (a line-of-sight movement, blinking, eyeball fixation, and a pupil diameter).

The driver state detection unit 3 includes, for example, an image sensor such as a CCD camera and a CMOS camera, for example, and detects a facial expression of the driver by photographing a face image of the driver. Further, the driver state detection unit 3 acquires a line-of-sight state (a line-of-sight movement, blinking, eyeball fixation, and a pupil diameter) detected by the eye camera 2. Further, the driver state detection unit 3 includes, for example, a heart rate sensor provided on a driver seat, and detects a heart rate of the driver. Further, the driver state detection unit 3 includes, for example, a heart rate sensor, or an image sensor such as a CCD camera and a CMOS camera, and detects a breathing state (a respiratory rate or a depth of breathing). The driver state detection unit 3 includes, for example, a resistance sensor, and detects a skin resistance. Further, the driver state detection unit 3 includes, for example, a pulse wave sensor provided on a steering wheel, and detects a fingertip pulse wave. The driver state detection unit 3 includes, for example, a 6-channel myoelectric sensor provided on the steering wheel, and detects EMG of the upper limb muscles. The driver state detection unit 3 includes, for example, a 3-channel myoelectric sensor provided on the driver seat, and detects EMG of the lower limb muscles. Further, the driver state detection unit 3 includes, for example, a microphone, and detects voice information. The voice information includes, for example, a tone of voice. The driver state detection unit 3 is, for example, constituted by a load sensor provided on the driver seat, and detects a seating pressure with respect to the driver seat.

The driver state detection unit 3 calculates an assessment value of a driver state by inputting a facial expression, a line-of-sight state, a heart rate, a breathing state, a skin resistance, a fingertip pulse wave, EMG of the upper limb muscles, EMG of the lower limb muscles, voice information, and a seating pressure described above in a predetermined mathematical expression for use in assessing the driver state. Then, the driver state detection unit 3 may detect a driver state from the assessment value. In this example, an assessment value indicating a degree of awakening may be used as the assessment value of the driver state. An assessment value, for example, increases in the plus direction, as a degree of awakening of a driver increases; and an assessment value increases in the minus direction, as a degree of absent-mindedness of a driver increases. Therefore, the driver state detection unit 3 may determine that a driver is awakened, when an assessment value is larger than a predetermined plus reference value, and may determine that a driver is absent-minded, when an assessment value is smaller than a predetermined minus reference value (is large in a minus direction). Note that a facial expression includes, for example, an expression of joy, an expression of anger, and an expression of sadness; and is quantified by predetermined numerical values with respect to these expressions. Further, the voice information includes joy, anger, sadness, and the like; and is quantified by predetermined numerical values with respect to these feelings.

The vehicle state detection unit 4 includes, for example, a vehicle speed sensor, and detects a speed of the own vehicle. Further, the vehicle state detection unit 4 includes, for example, a speed sensor for detecting an engine speed, and detects the engine speed. Further, the vehicle state detection unit 4 includes, for example, a steering angle sensor, and detects a steering angle of the wheels. Further, the vehicle state detection unit 4 includes, for example, a wiper operation sensor for detecting an operating condition of a wiper, and detects the operating condition of the wiper. Note that the operating condition of the wiper is used for detecting a weather (e.g. a rainy weather or a snowy weather). Further, the vehicle state detection unit 4 includes, for example, a light sensor for detecting an operating condition of a light mounted in the own vehicle, and detects the operating condition of the light. Note that the operating condition of the light is used for detecting the day and night, for example.

The navigation device 5 includes a GPS sensor, and a processor for searching a route to a destination. The navigation device 5 acquires road information relating to conditions of a road on which the own vehicle is currently traveling, and road conditions ahead of the own vehicle. The road information to be acquired in this example includes, for example, information relating to a highway, an open road, a straight road, a curved road, an intersection, contents of various types of road signs, presence of a traffic signal, and current position information of the own vehicle.

As will be described later, the controller U controls the projection mapping device 11, the head-up display 12, and the speaker 13 in order to guide a line-of-sight of the driver toward a visual perception target (an overlooked visual perception target), which may be overlooked by the driver.

The controller U includes a visual perception target determination unit 24 and a visual guidance unit 25. The visual perception target determination unit 24 determines a visual perception target that the driver should visually perceive by using three types of visual perception models i.e. a saliency model 21, a surprise model 22, and a normative model 23. The saliency model 21 includes data for determining that an object having saliency and the driver can visually perceive at a glance, as a visual perception target. An object to be detected by using the saliency model 21 is, for example, an object of a relatively large size, an object of a relatively large brightness, an object in which the contrast is relatively strong, and an object of a unique shape, among objects to be visually perceived by the driver during driving. Numerous pieces of data for use in detecting an object to be visually perceived at a glance are stored in the saliency model 21.

The surprise model 22 includes data for determining an object behaving abnormally (action against which precautions are required) as a visual perception target. The surprise model 22 includes, for example, data for determining an object such as a vehicle and a pedestrian behaving abnormally, as a visual perception target. Numerous pieces of data for use in detecting an object such as a vehicle, a pedestrian, and a motorcycle, which may behave abnormally, and data for use in detecting that each object behaves abnormally are stored in the surprise model 22 in association with each other.

The normative model 23 includes data for determining that an object to be visually perceived by a viewing action of a skillful driver serving as a norm is a visual perception target. A target the driver should look at, a position the driver should look at, an order of objects in which the driver should look at, and the like are stored in the normative model 23 in association with numerous traveling conditions (combinations of traveling environments including surrounding conditions, vehicle states, and the like).

The visual guidance unit 25 determines whether or not an overlooked visual perception target to which a line-of-sight direction to be detected by the eye camera 2 is not directed is present among visual perception targets determined by the visual perception target determination unit 24. When an overlooked visual perception target is present, the visual guidance unit 25 guides a line-of-sight of the driver toward the overlooked visual perception target. The visual guidance unit 25 may guide the line-of-sight by using the projection mapping device 11, the head-up display 12, and the speaker 13.

Figure 2:
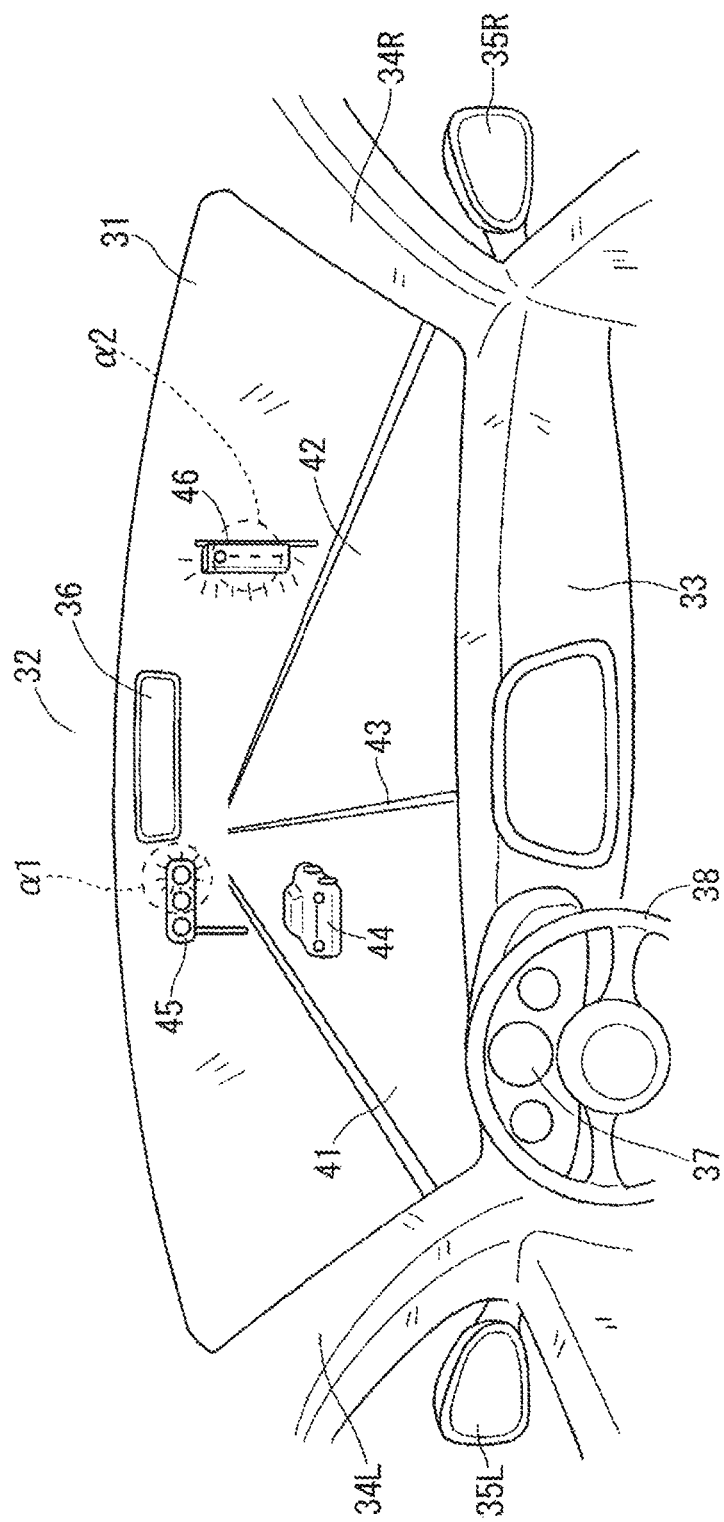
FIG. 2 is a diagram for describing how a visual perception target is determined by a saliency model.

The aforementioned three types of visual perception models are described one by one by using an automobile as an example. FIG. 2 illustrates a surrounding condition when the driver looks ahead from a vehicle compartment of the own vehicle. An upper peripheral portion (upper frame portion) of a front window glass 31 is defined by a front peripheral portion of a roof panel 32, a lower peripheral portion (lower frame portion) of the front window glass 31 is defined by a front peripheral portion of an instrument panel 33, a left peripheral portion (left frame portion) of the front window glass 31 is defined by a left front pillar 34L, and a right peripheral portion (right frame portion) of the front window glass 31 is defined by a right front pillar 34R.

In FIG. 2, a left side mirror 35L is disposed on the left side of the front pillar 34L, and a right side mirror 35R is disposed on the right side of the front pillar 34R. A rearview mirror 36 is disposed on the upper side in the middle of the front window glass 31 in the vehicle width direction. A meter panel 37 is disposed on the left side of the instrument panel 33. A steering wheel 38 to be operated by the driver when the driver operates the own vehicle is disposed on the front side of the instrument panel 38. In the example of FIG. 2, a left-hand drive car is used as the own vehicle. This is merely an example. A right-hand drive car may be used.

In FIG. 2, as road conditions ahead of the own vehicle to be visually perceived by the driver through the front window glass 31, a driving lane 41 along which the driver drives the own vehicle, an opposite lane 42, a center divider 43 indicating a boundary between the driving lane 41 and the opposite lane 42 are illustrated. A preceding vehicle 44 is present on the driving lane 41, a traffic light 45 is present ahead of the preceding vehicle 44, and a blinking signboard 46 is present along a berm of the opposite lane 42.

In the saliency model 21, an object to be visually perceived at a glance is determined to be a visual perception target. Therefore, for example, in the example of FIG. 2, the traffic light 45 and the blinking signboard 46 are determined to be visual perception targets. In the saliency model 21, when a stop lamp of the preceding vehicle 44 is turned on, the preceding vehicle 44 in which the stop lamp is turned on is also determined to be a visual perception target.

It is highly likely that a visual perception target to be determined by the saliency model 21 is visually perceived by the driver. Therefore, even when the line-of-sight direction of the driver does not completely coincide with a direction in which a visual perception target determined by the saliency model 21 is present, it is determined that the driver visually perceives the visual perception target, when the line-of-sight direction of the driver is directed toward the visual perception target to some extent. In the example of FIG. 2, even when the line-of-sight direction of the driver does not completely coincide with a direction in which the traffic light 45 or the signboard 46 determined as a visual perception target by the saliency model 21 is present, it is determined that the driver visually perceives the traffic light 45 or the signboard 46, when the line-of-sight direction of the driver is directed toward the traffic light or the signboard 46 to some extent.

In this example, the expression "completely coincide" means that a visual perception target and a line-of-sight direction intersect each other, for example. Further, the expression "the line-of-sight direction of the driver is directed toward the visual perception target to some extent" means that the visual perception target is present within a field of view including the line-of-sight direction as a center. The visual guidance unit 25 may set, as a field of view, a substantially conical area, which is determined in advance and includes a line-of-sight direction as a center.

On the other hand, when a line-of-sight direction of the driver is largely deviated from the traffic light 45, and it is judged that the driver does not visually perceive the traffic light 45, the traffic light 45 is determined to be an overlooked visual perception target. In this case, for example, an index α1 indicated by a round shape of a dotted line is projected toward the traffic light 45 by the projection mapping device 11 disposed within the vehicle compartment. Then, the index α1 is displayed on the front window glass 31 in such a manner that the index α1 overlaps the traffic light 45 at a position of the traffic light 45, and the light-of-sight of the driver is guided to the index α1. Note that the expression "largely deviated" means that a visual perception target is present outside the field of view, for example.

Likewise, when it is determined that the driver does not visually perceive the signboard 46, an index α2 is projected toward the signboard 46. The index α2 is displayed on the front window glass 31 in such a manner that the index α2 overlaps the signboard 46 at a position of the signboard 46.

Note that the index α1 or the index α2 may be displayed by using the head-up display 12 disposed at a front position of the driver, for example. Further, a voice guide such as "pay attention to the traffic light on the left side!" or "pay attention to the signboard on the right side!" may be output from the speaker 13, for example. The visual perception targets illustrated in FIG. 2 are merely an example. Numerous pieces of data for use in detecting visual perception targets, which are likely to be memorized at a glance, are stored in the saliency model 21 in advance.

As will be described later, an object that the driver does not have to look at may be eliminated from visual perception targets. For example, the signboard 46 may be eliminated from visual perception targets. In this case, an object that should be eliminated may be stored in the saliency model 21 itself. Alternatively, a visual perception target that meets a predetermined elimination condition may be removed from visual perception targets determined by the saliency model 21. In this example, as the predetermined condition, for example, it is possible to use a condition that a visual perception target determined by the saliency model 21 is away from the own vehicle by a predetermined distance or more, and a condition that a visual perception target is a fixed object located on the side of the opposite lane.

Figure 3:
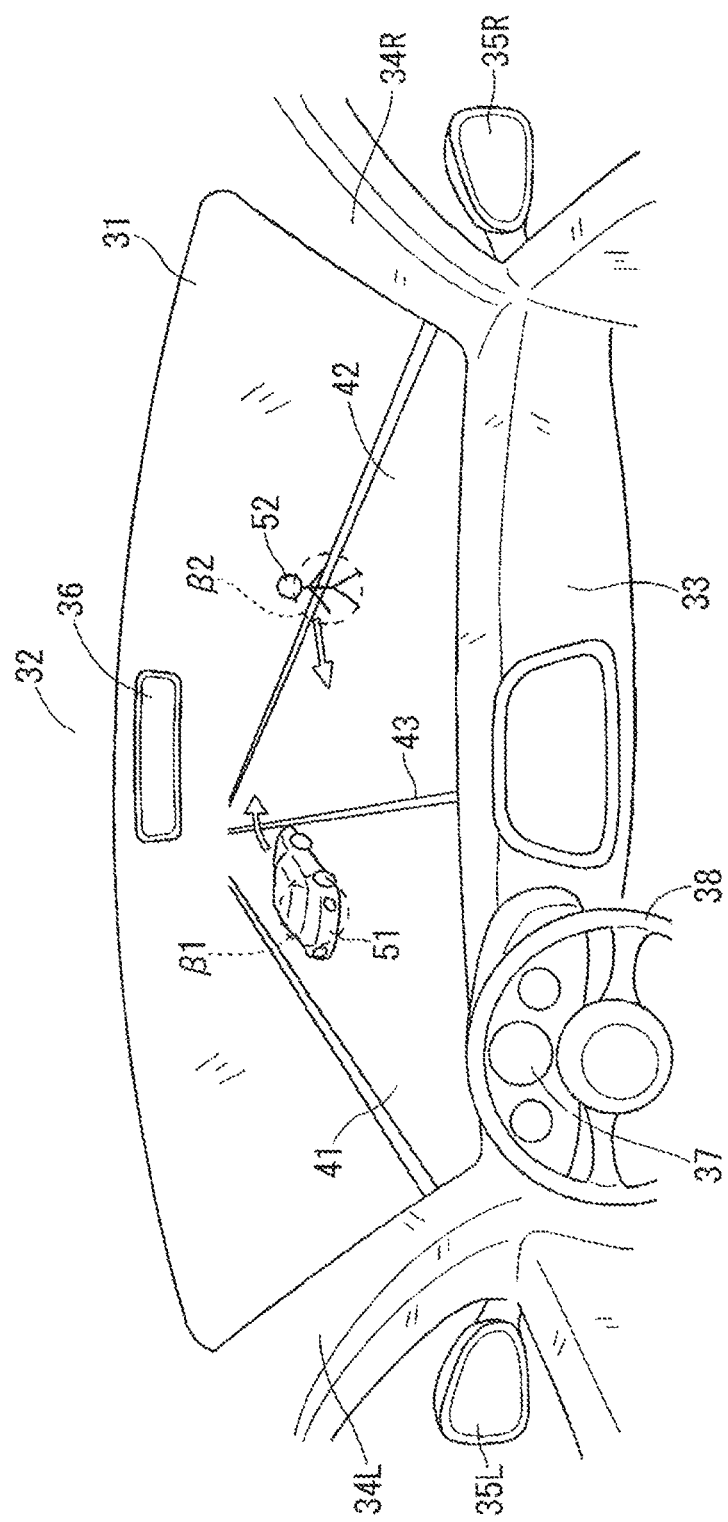
FIG. 3 is a diagram for describing how a visual perception target is determined by a surprise model.

Next, the surprise model 22 is described with reference to FIG. 3. As well as FIG. 2, FIG. 3 illustrates a surrounding condition when the driver looks ahead from the vehicle compartment of the own vehicle. FIG. 3 illustrates a condition in which a preceding vehicle 51 behaves abnormally i.e. the preceding vehicle 51 is suddenly moving toward the opposite lane 42. Further, FIG. 3 illustrates a condition in which a pedestrian 52 trespasses the opposite lane 42 from the side of a berm of the opposite lane 42, and is walking toward the driving lane 41. Since the preceding vehicle 51 and the pedestrian 52 behave abnormally (action against which precautions are required), the preceding vehicle 51 and the pedestrian 52 are determined to be visual perception targets in the surprise model 22. When a line-of-sight direction of the driver is not directed toward the preceding vehicle 51, an index $\beta 1$ is projected toward the preceding vehicle 51. Then, the index $\beta 1$ is displayed on the front window glass 31 in such a manner that the index $\beta 1$ overlaps the preceding vehicle 51 at a position of the preceding vehicle 51. Likewise, when a line-of-sight direction of the driver is not directed toward the pedestrian 52, the index $\beta 2$ is projected toward the pedestrian 52. Then, the index $\beta 2$ is displayed on the front window glass 31 in such a manner that the index $\beta 2$ overlaps the pedestrian 52 at a position of the pedestrian 52. In the embodiment, an alert by the head-up display 12 or the speaker 13 may be issued together with display of the index $\beta 1$ and the index $\beta 2$ in a similar manner to the case described with reference to FIG. 2. In this example, the visual guidance unit 25 may determine that a line-of-sight direction of the driver is directed toward a visual perception target, when the visual perception target is present within the field of view of the driver, for example.

Figure 4:
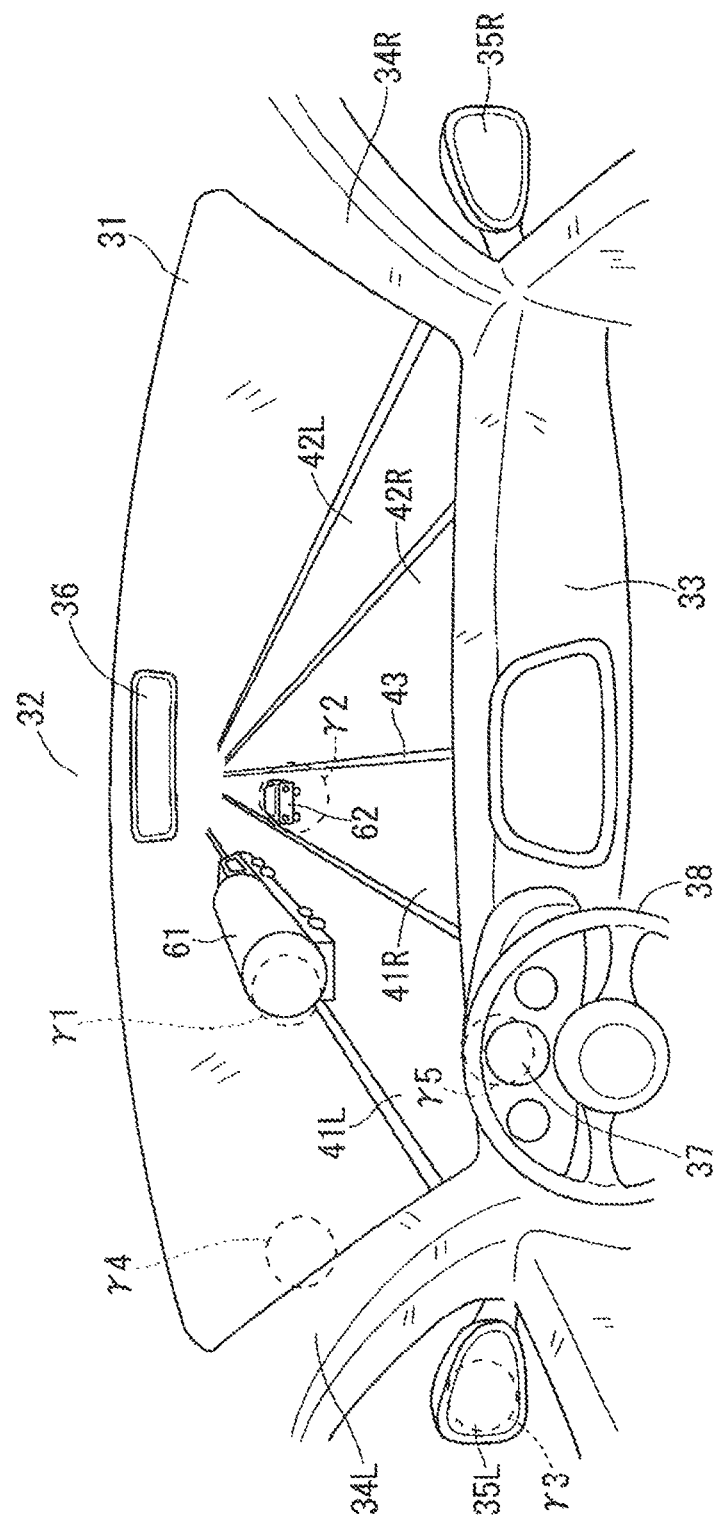
FIG. 4 is a diagram for describing how a visual perception target is determined by a normative model.

Next, the normative model 23 is described with reference to FIG. 4. FIG. 4 illustrates a surrounding condition when the driver looks ahead from the vehicle compartment of the own vehicle, as well as FIG. 2. In FIG. 4, however, the own vehicle is traveling on a two-lane road, and specifically, is traveling on a driving lane 41R, which is second from the left. A lane on the left side of the driving lane 41R is a left driving lane 41L. Opposite lanes 42R and 42L are present on the right of the driving lane 41R in this order. The driving lane 41R and the opposite lane 42R are separated by a center divider 43. In the driving lane 41R, a preceding vehicle 62 being a small-sized vehicle (e.g. a passenger car) is traveling ahead of the own vehicle, and a large-sized vehicle (a tank lorry in FIG. 4) 61 is traveling on the left driving lane 41L.

FIG. 4 illustrates that the own vehicle, the preceding vehicle 62, and the vehicle 61 ahead on the left side continue stable traveling i.e. steady running, and are not in a condition that particular precautions are required. In this condition, the normative model 23 determines a visual perception target, based on a viewing action of a skillful driver serving as a norm. In this example, the preceding vehicle 62 and the vehicle 61 ahead on the left side are determined as visual perception targets. In view of the above, the visual guidance unit 25 projects an index $\gamma 1$ toward the vehicle 61 ahead on the left side, and projects an index $\gamma 2$ toward the preceding vehicle 62 by using the projection mapping device 11. Thus, the index $\gamma 1$ and the index $\gamma 2$ are displayed on the front window glass 31 in such a manner that the index $\gamma 1$ and the index $\gamma 2$ overlap the vehicle 61 ahead on the front side and the preceding vehicle 62 at positions of the vehicle 61 ahead on the front side and the preceding vehicle 62.

Further, a left side mirror 35L for use in perceiving a condition on the left side, an intermediate portion of a left peripheral portion of the front window glass 31 in the up-down direction which is likely to become a blind spot, and a meter panel 37 for use in checking the vehicle speed and the like are determined to be visual perception targets. Therefore, the visual guidance unit 25 projects an index $\gamma 3$ toward the left side mirror 35L, projects an index $\gamma 4$ toward the intermediate portion of the left peripheral portion of the front window glass 31, and projects an index $\gamma 5$ toward the meter panel 37 by using the projection mapping device 11.

The normative model 23 stores data indicating objects to be visually perceived by a viewing action of a skillful driver serving as a norm, and data indicating positions of the objects in all possible (numerous) conditions. Further, the normative model 23 also stores a cycle at which the driver should visually perceive. For example, when it is assumed that a skillful driver looks at the left side mirror 35L at least once per ten seconds, for example, data such that once per ten seconds for the left side mirror 35L are used as a cycle at which the driver should visually perceive.

In FIG. 4, the indexes $\gamma 1$ to $\gamma 5$ are displayed when a line-of-sight direction of the driver is not directed toward a visual perception target determined by the normative model 23. Note that FIG. 4 is merely an example. As visual perception targets, the rearview mirror 36 and the right side mirror 35R may be included as visual perception targets to be determined by the normative model 23. Further, a viewing order and a viewing cycle may be stored in the normative model 23, and the viewing order and the viewing cycle may be determined depending on a visual perception target.

In this example, when the driver state detection unit 3 detects that driving load of the driver is large or that the driver is absent-minded, the visual guidance unit 25 may emphasize visual guidance. For example, in FIG. 2 to FIG. 4, when the indexes $\alpha 1$, $\alpha 2$, $\beta 1$, $\beta 2$, and $\gamma 1$ to $\gamma 5$ are displayed (projected) faintly in a normal condition, for example, the visual guidance unit 25 may display the indexes $\alpha 1$, $\alpha 2$, $\beta 1$, $\beta 2$, and $\gamma 1$ to $\gamma 5$ clearly as compared with the normal condition. Alternatively, when the indexes $\alpha 1$, $\alpha 2$, $\beta 1$, $\beta 2$, and $\gamma 1$ to $\gamma 5$ are displayed in an on-state in a normal condition, for example, the visual guidance unit 25 may display the indexes $\alpha 1$, $\alpha 2$, $\beta 1$, $\beta 2$, and $\gamma 1$ to $\gamma 5$ in a blinking manner. Alternatively, when the indexes $\alpha 1$, $\alpha 2$, $\beta 1$, $\beta 2$, and $\gamma 1$ to $\gamma 5$ are displayed with an achromatic color such as white or black in a normal condition, for example, the visual guidance unit 25 may display the indexes $\alpha 1$, $\alpha 2$, $\beta 1$, $\beta 2$, and $\gamma 1$ to $\gamma 5$ with a clearly perceivable color of a high saturation (e.g. red or green), as compared with the normal condition.

In addition to the above, the visual guidance unit 25 may emphasize visual guidance by using the head-up display 12 and the speaker 13, in addition to the projection mapping device 11. Note that the driver state detection unit 3 may determine a magnitude of driving load by adding a magnitude of the number of overlooked visual perception targets, a degree of difficulty of a traveling environment, or the like. For example, when the number of overlooked visual perception targets is larger than a predetermined threshold value, the driver state detection unit 3 may determine that driving load is large. When the number of overlooked visual perception targets is equal to or smaller than the predetermined threshold value, the driver state detection unit 3 may determine that driving load is small.

Further, the driver state detection unit 3 may calculate, for example, a degree of difficulty of a traveling environment, based on road conditions around the own vehicle acquired from the navigation device 5, and the number of visual perception targets. When the degree of difficulty is larger than a predetermined threshold value, the driver state detection unit 3 may determine that driving load is large; and when the degree of difficulty is equal to or smaller than the predetermined threshold value, the driver state detection unit 3 may determine that driving load is small. A degree of difficulty may be calculated, for example, by using a predetermined function, in which a large value is output, as the number of visual perception targets increases, and a value depending on a type of road conditions is output. As the value depending on a type of road conditions, for example, a value such that an intersection is larger than a straight road may be used.

Figure 5:
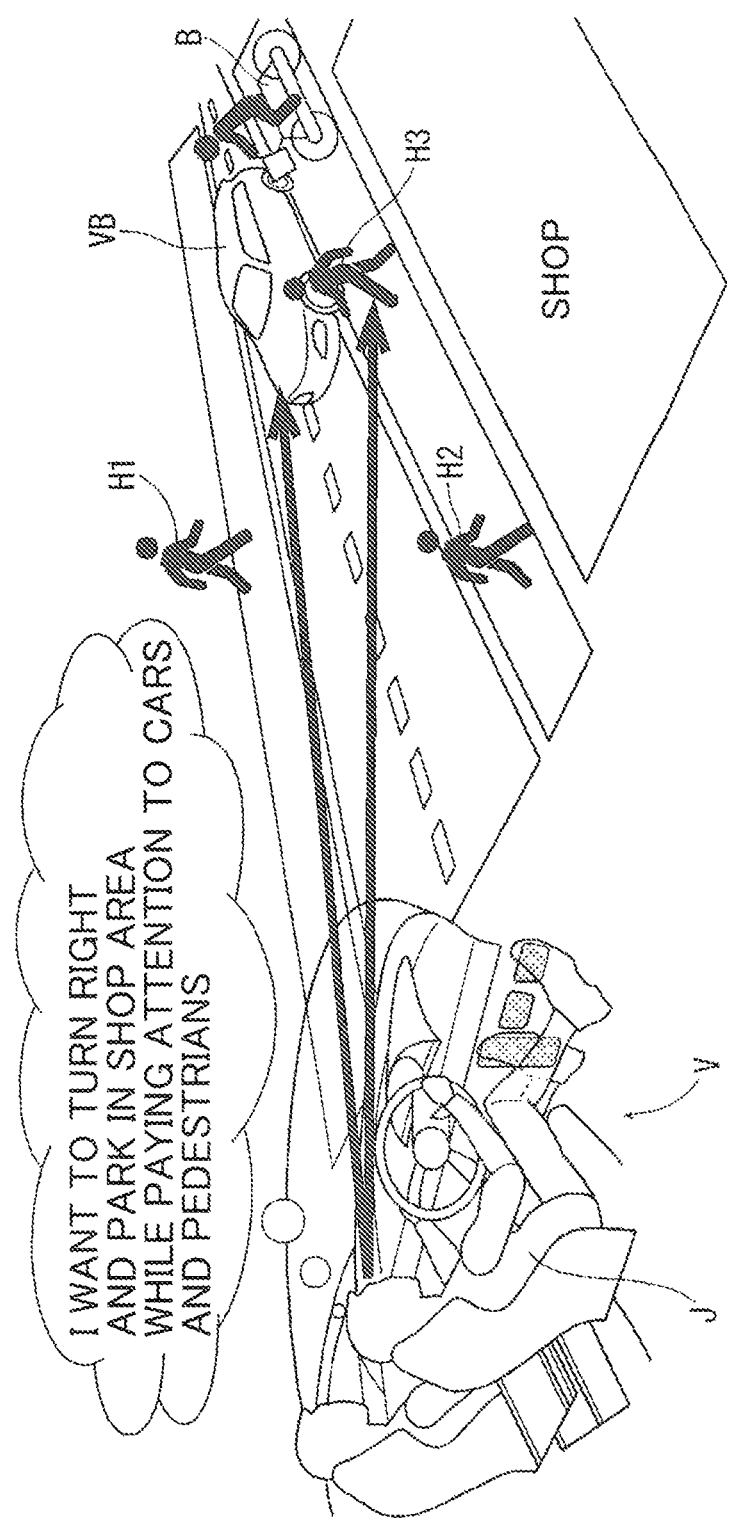
FIG. 5 is a diagram illustrating a condition in which a visual perception target is overlooked when driving load is large.

FIG. 5 illustrates a condition in which an own vehicle V tries to park in a shop area (e.g. a convenience store) across an opposite lane. In FIG. 5, an oncoming vehicle VB, pedestrians H1 to H3, and a motorcycle B are present in a direction of movement of the own vehicle V. A driver J of the own vehicle V tries to park in the shop area, while paying attention to the oncoming vehicle VB and the pedestrian H3 on a side of the oncoming vehicle VB. Since driving load is large, the line-of-sight of the driver J is not directed toward the motorcycle B. The driver J does not notice the motorcycle B behind the oncoming vehicle VB.

In this case, the visual perception target determination unit 24 determines the motorcycle B as a visual perception target by using the aforementioned three types of visual perception models. Since the line-of-sight of the driver J is not directed toward the motorcycle B, which is determined to be a visual perception target, the visual guidance unit 25 determines the motorcycle B as an overlooked visual perception target. Then, the visual guidance unit 25 projects an index toward the motorcycle B. Thus, the index is displayed at a position on the front window glass 31 associated with the motorcycle B, and the line-of-sight of the driver J is guided to the motorcycle B.

In this case, since the driver is absent-minded, the visual guidance unit 25 may increase a degree of emphasis of visual guidance, as compared with a case where the driver is in a normal condition. For example, the visual guidance unit 25 may display an index clearly, may display an index in a blinking manner, or may display an index with a color of a high saturation, as compared with an ordinary display pattern.

Figure 6:
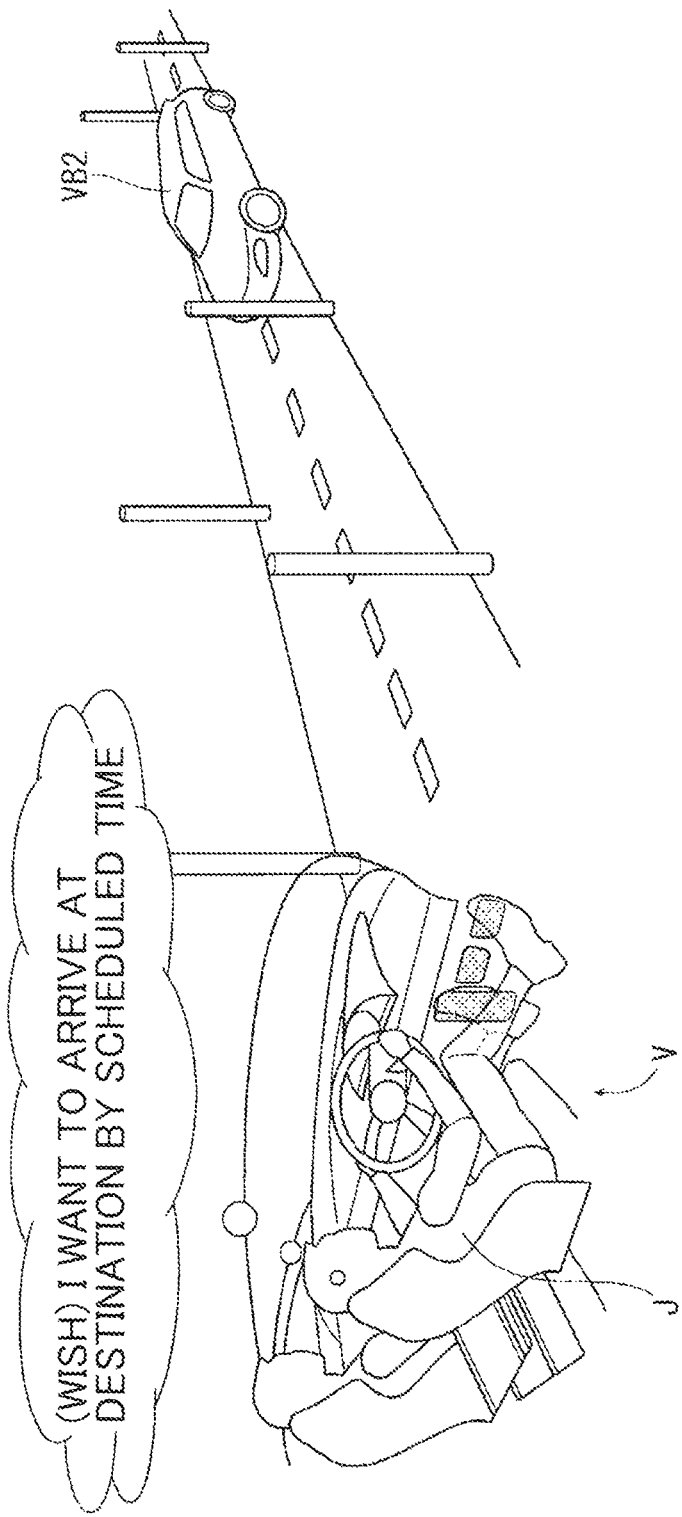
FIG. 6 is a diagram illustrating a condition in which a visual perception target is overlooked when a driver is absent-minded.

FIG. 6 illustrates a condition in which the own vehicle V is traveling on a suburb road of monotonous landscape where a surrounding condition hardly changes. The driver J is preoccupied with an idea as to whether he/she will arrive at a destination by a scheduled meeting time, and what he/she should do after arriving at the destination. Therefore, the driver J may be absent-minded and may not notice a surrounding condition carefully. FIG. 6 illustrates a condition that an oncoming vehicle VB2 is closely approaching the own vehicle V. In this case, a possibility that the driver J may overlook the oncoming vehicle VB2, which is not overlooked when the driver J is awakened, is high. In this case, the visual perception target determination unit 24 is able to determine that the oncoming vehicle VB2 is a visual perception target by using the three types of visual perception models. The visual guidance unit 25 projects an index or an emphasized index toward the oncoming vehicle VB2. Thus, the index is displayed at a position on the front window glass 31 associated with the oncoming vehicle VB2, and the driver J can perceive the presence of the oncoming vehicle VB2.

Note that the driver state detection unit 3 may determine whether or not the own vehicle is traveling in a suburb area of monotonous landscape by using a current position of the vehicle and road conditions acquired from the navigation device 5, and a vehicle speed detected by the vehicle state detection unit 4, and the like.

Next, a control example by the controller U is described with reference to the flowchart illustrated in FIG. 7. In the following description, Q indicates a step. First of all, in Q1, the driver state detection unit 3 detects a driver state by using a line-of-sight state detected by the eye camera 2, a facial expression of the driver detected by an image sensor, and the like. Further, in Q1, the vehicle state detection unit 4 detects a vehicle state, and the navigation device 5 detects road conditions and a current position of the own vehicle.

In Q2, the camera 1 acquires an image indicating a surrounding condition ahead of the own vehicle by photographing an area ahead of the own vehicle.

In Q3, the visual perception target determination unit 24 applies the saliency model 21 to the image acquired in Q2, and determines a visual perception target. In Q4, the visual perception target determination unit 24 applies the surprise model 22 to the image acquired in Q2, and determines a visual perception target. In Q5, the visual perception target determination unit 24 applies the normative model 23 to the image acquired in Q2, and determines a visual perception target.

In Q6, the visual perception target determination unit 24 collects the visual perception targets determined in Q3 to Q5. In Q6, the visual perception target determination unit 24 also performs processing of eliminating an object that the driver does not have to look at from the visual perception targets determined in Q3 to Q5. For example, an object far from the own vehicle, and a fixed object to which the driver does not have to pay attention are eliminated from the visual perception targets.

In Q7, the eye camera 2 detects a line-of-sight direction of the driver.

In Q8, the visual guidance unit 25 determines whether or not a visual perception target outside the field of view of the driver is present among the visual perception targets collected in Q6. When a visual perception target outside the field of view is present, the visual guidance unit 25 extracts the visual perception target as an overlooked visual perception target. More specifically, the visual guidance unit 25 records a line-of-sight direction of the driver for a predetermined period in the past. Then, the visual guidance unit 25 may set a field of view for each of the recorded line-of-sight directions, and may determine a visual perception target outside the set field of view, as an overlooked visual perception target, among the visual perception targets collected in Q6. Note that even when the entirety of a visual perception target is not present in a field of view, the visual guidance unit 25 may determine that the driver successfully visually perceives the visual perception target when a part of the visual perception target is present in the field of view.

In Q9, when an overlooked visual perception target is not present (NO in Q9), the visual guidance unit 25 returns the processing to Q1. On the other hand, when an overlooked visual perception target is present (YES in Q9), the processing is proceeded to Q10.

In Q10, the driver state detection unit 3 determines whether or not a driver state is such that driving load is large. When the driver state is such that driving load is large (YES in Q10), the visual guidance unit 25 sets visual guidance to "emphasis is set" (Q11).

On the other hand, when the driver state is such that driving load is not large (NO in Q10), the driver state detection unit 3 determines whether or not the driver is absent-minded (Q12). When the driver is absent-minded (YES in Q12), the visual guidance unit 25 sets visual guidance to "emphasis is set" (Q11).

When the driver is not absent-minded (NO in Q12), the visual guidance unit 25 sets visual guidance to "emphasis is not set" (Q13).

In Q14, the visual guidance unit 25 determines whether or not a plurality of overlooked visual perception targets are present. When the number of overlooked visual perception targets is one (NO in Q14), the visual guidance unit 25 projects an index (e.g. the index α1 in FIG. 2, the index β1 in FIG. 3) for use in guiding a line-of-sight toward the overlooked visual perception target (Q15). In this case, the visual guidance unit 25 displays the index in an emphasized manner when "emphasis set" is set in Q11, and displays the index in a normal manner when "emphasis is not set" is set in Q13.

On the other hand, when a plurality of overlooked visual perception targets are present in Q14 (YES in Q14), the visual guidance unit 25 ranks the plurality of overlooked visual perception targets in guiding a line-of-sight (Q16). In this case, the visual guidance unit 25 may rank objects in a descending order of a degree of hazard or a degree of caution. Further, the visual guidance unit 25 may rank objects in an ascending order of a distance from the own vehicle. For example, the visual guidance unit 25 may give, to each of a plurality of overlooked visual perception targets, a point such that a value thereof increases as a degree of hazard increases, a value thereof increases as a degree of caution increases, and a value thereof increases as a distance from the own vehicle decreases; and may rank visual perception targets in a descending order of a point. The point depending on a degree of hazard and a degree of caution may be set such that a value thereof is set depending on a type of object set in advance. For example, a point may be set high for a pedestrian crossing a road than a pedestrian walking on a sidewalk.

In Q17, the visual guidance unit 25 displays indexes (e.g. the index α1 in FIG. 2, and an index β1 in FIG. 3) on a plurality of overlooked visual perception targets in the ranking set in Q16. In this case, when "emphasis is set" is set in Q11, the visual guidance unit 25 displays the indexes in an emphasized manner; and when "emphasis not set" is set in Q13, the visual guidance unit 25 displays the indexes in a normal manner. As a display pattern on ranking, a pattern may be such that indexes are displayed for overlooked visual perception targets in a descending order of ranking. For example, an index associated with an overlooked visual perception target at a first place may be displayed first, an index associated with an overlooked visual perception target at a second place may be displayed after lapse of a predetermined time (e.g. from 1 to 5 seconds), and then, an index associated with an overlooked visual perception target at a third place may be displayed after lapse of a predetermined time.

When a plurality of overlooked visual perception targets are present (YES in Q14), the visual guidance unit 25 may simultaneously display indexes associated with the plurality of overlooked visual perception targets without ranking. When Q15 and Q17 are terminated, the processing returns to Q1.

In the foregoing, an embodiment is described. The present invention, however, is not limited to the embodiment. Modifications are applicable as necessary within the scope of the claims. A vehicle constituted by a four-wheel automobile is exemplified as a moving body to be driven by a driver. This is merely an example. As the moving body, for example, vehicles (e.g. a motorcycle) other than a four-wheel automobile, various construction machines and machinery for construction work, transport machinery such as a forklift, which is frequently used in a factory or a construction site, vessels (particularly, small vessels), and airplanes (particularly, small airplanes) may be used. Further, the moving body may be a moving body (e.g. a drone or a helicopter), which is remotely controlled by an operator. Further, the moving body and the surrounding condition may be virtual. For example, a driving simulator corresponds to a virtual moving body or surrounding environment.

The aforementioned visual perception assistance system is applied to a moving body. The present invention, however, is not limited to the above. The present invention may be directed to a detection system for detecting a visual perception target that an operator should look at in a construction site. Further, the present invention may be directed to a detection system for detecting a visual perception target that an observer should look at in an inspection process in a factory. Further, the present invention may be applied to assessing the interior of a shop, and the like.

Specifically, the present invention may be directed to a detection system for detecting a visual perception target that an observer should look at by using the three visual perception models in a place other than a place where a moving body is used. In this case, in FIG. 1, the driver state detection unit 3, the vehicle state detection unit 4, and the navigation device 5 may be omitted.

In a detection system, visual guidance may be performed by displaying a direction of an overlooked visual perception target by the head-up display 12 (an example of a display unit), in place of displaying an index at a position of an overlooked visual perception target. Further, in a detection system, visual guidance may be performed by audio guidance in which a direction of an overlooked visual perception target is guided by the speaker 13. In a detection system, an observer in a stationary state corresponds to a driver of a visual perception assistance system.

Figure 7:
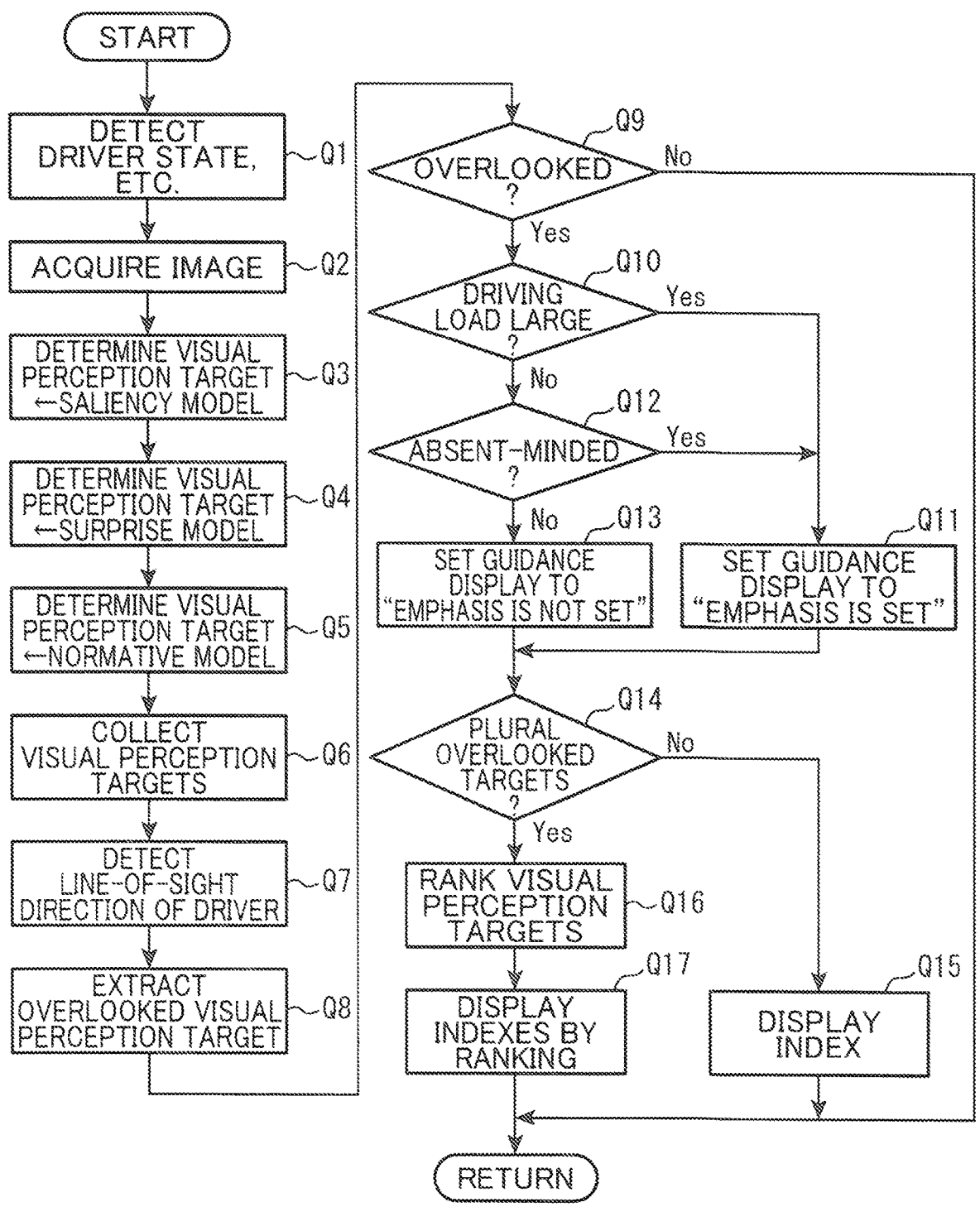
FIG. 7 is a flowchart illustrating a control example according to the present invention.

Each step or a group of steps illustrated in FIG. 7 may be regarded as a function of the controller U or means for exhibiting the function. It is needless to say that an object of the present invention is not limited to an explicitly described one, and may implicitly include providing what is expressed as a substantially preferred embodiment or an advantage.

SUMMARY OF EMBODIMENT

The following is a summary of technical features of the embodiment.

A visual perception assistance system according to an aspect of the present invention includes:

a surrounding condition acquisition unit for acquiring a surrounding condition of a moving body to be driven by a driver;

a visual perception target determination unit for determining a visual perception target being an object that the driver should look at in a surrounding condition acquired by the surrounding condition acquisition unit;

a line-of-sight direction detection unit for detecting a line-of-sight direction of the driver; and a visual guidance unit for determining whether or not an overlooked visual perception target to which a line-of-sight direction detected by the line-of-sight direction detection unit is not directed is present among the visual perception target determined by the visual perception target determination unit, and guiding a line-of-sight of the driver toward the overlooked visual perception target, when the overlooked visual perception target is present, wherein the visual perception target determination unit determines the visual perception target, based on three visual perception models prepared in advance, and the three visual perception models include a saliency model for determining that an object to be visually perceived at a glance is a visual perception target, a surprise model for determining that an object behaving abnormally is a visual perception target, and a normative model for determining that an object to be visually perceived by a viewing action of a driver serving as a norm is a visual perception target.

According to the aforementioned configuration, it is possible to securely determine the visual perception target that the driver should visually perceive by using the three visual perception models. Further, in the aforementioned configuration, since the line-of-sight of the driver is guided toward the overlooked visual perception target, it is possible to prevent overlooking of the visual perception target.

In the aforementioned configuration, the moving body may be constituted by a vehicle, and the surrounding condition acquisition unit may be constituted by a camera for photographing an area ahead of the vehicle.

In this case, it is possible to prevent overlooking of the visual perception target when the driver drives the vehicle, and implement safety driving of the vehicle.

In the aforementioned configuration, the visual guidance unit may perform visual guidance by displaying an index at a position of the overlooked visual perception target.

In this case, since the index is displayed at the position of the overlooked visual perception target, it is possible to securely perform visual guidance.

In the aforementioned configuration, the visual perception assistance system may further include a driver state detection unit for detecting the driver state, wherein the visual guidance unit may change a degree of intensity of visual guidance depending on a driver state to be detected by the driver state detection unit.

In this case, it is possible to more accurately perform visual guidance by changing the degree of intensity of visual guidance depending on the driver state.

In the aforementioned configuration, the visual guidance unit may change the degree of intensity of visual guidance by changing a degree of conspicuousness of an index to be displayed at a position of the overlooked visual perception target.

In this case, since the index is displayed at the position of the overlooked visual perception target, it is possible to securely perform visual guidance. Further, it is possible to more accurately perform visual guidance by changing the degree of intensity of visual guidance depending on the driver state.

In the aforementioned configuration, the driver state detection unit may detect at least a state that driving load is large as the driver state, and when the driver state detection unit detects that the driving load is large, the visual guidance unit may emphasize visual guidance, as compared with a case where the driver state detection unit detects that the driving load is small.

In this case, it is possible to securely guide the line-of-sight of the driver toward the overlooked visual perception target, when the driving load is large i.e. overlooking of the visual perception target is likely to occur.

In the aforementioned configuration, the driver state detection unit may detect at least a state that the driver is absent-minded, as the driver state, and when the driver state detection unit detects that the driver is absent-minded, the visual guidance unit may emphasize visual guidance, as compared with a case where the driver state detection unit detects that the driver is not absent-minded.

In this case, it is possible to securely guide the line-of-sight of the driver toward the overlooked visual perception target, when the driver is absent-minded i.e. overlooking of the visual perception target is likely to occur.

In the aforementioned configuration, when a plurality of the overlooked visual perception targets are present, the visual guidance unit may rank the plurality of overlooked visual perception targets in a viewing order, and may perform visual guidance of the plurality of overlooked visual perception targets by the ranking.

In this case, when a plurality of overlooked visual perception targets are present, since visual guidance of the overlooked visual perception targets is performed by the ranking, it is possible to perform visual guidance in a descending order of importance with respect to the visual perception targets, for example.

A visual perception target detection system according to another aspect of the present invention may include:

a surrounding condition acquisition unit for acquiring a surrounding condition of an observer; and a visual perception target determination unit for determining a visual perception target being an object that the observer should look at in a surrounding condition acquired by the surrounding condition acquisition unit, wherein the visual perception target determination unit may determine the visual perception target, based on three visual perception models prepared in advance, and the three visual perception models may include a saliency model for determining that an object to be visually perceived at a glance is a visual perception target, a surprise model for determining that an object behaving abnormally is a visual perception target, and a normative model for determining that an object to be visually perceived by a viewing action of an observer serving as a norm is a visual perception target.

According to the aforementioned configuration, it is possible to securely detect the visual perception target that the observer should look at.

In the aforementioned configuration, the visual perception target detection system may further include a display unit for displaying a visual perception target determined by the visual perception target determination unit.

In this case, the observer is able to easily and clearly grasp an object which may be overlooked but the observer should pay attention to.

INDUSTRIAL APPLICABILITY

The present invention is advantageous in the field of automobiles, or in the field of monitoring a construction site and a factory, since it is possible to prevent overlooking of a visual perception target.

The invention claimed is:

1. A visual perception assistance system, comprising:
a surrounding condition acquisition unit for acquiring a surrounding condition of a moving body to be driven by a driver;
a visual perception target determination unit for determining a visual perception target being an object that the driver should look at in a surrounding condition acquired by the surrounding condition acquisition unit;
a line-of-sight direction detection unit for detecting a line-of-sight direction of the driver; and
a visual guidance unit for determining whether or not an overlooked visual perception target to which a line-of-sight direction detected by the line-of-sight direction detection unit is not directed is present among the visual perception target determined by the visual perception target determination unit, and guiding a line-of-sight of the driver toward the overlooked visual perception target, when the overlooked visual perception target is present, wherein
the visual perception target determination unit determines the visual perception target, based on three visual perception models prepared in advance, and
the three visual perception models include a saliency model for determining that an object to be visually perceived at a glance is a visual perception target, a surprise model for determining that an object behaving abnormally is a visual perception target, and a normative model for determining that an object to be visually perceived by a viewing action of a driver serving as a norm is a visual perception target.

2. The visual perception assistance system according to claim 1, wherein
the moving body is constituted by a vehicle, and
the surrounding condition acquisition unit is constituted by a camera for photographing an area ahead of the vehicle.

3. The visual perception assistance system according to claim 1, wherein
the visual guidance unit performs visual guidance by displaying an index at a position of the overlooked visual perception target.

4. The visual perception assistance system according to claim 1, further comprising:
a driver state detection unit for detecting the driver state, wherein
the visual guidance unit changes a degree of intensity of visual guidance depending on a driver state to be detected by the driver state detection unit.

5. The visual perception assistance system according to claim 4, wherein
the visual guidance unit changes the degree of intensity of visual guidance by changing a degree of conspicuousness of an index to be displayed at a position of the overlooked visual perception target.

6. The visual perception assistance system according to claim 4, wherein
the driver state detection unit detects at least a state that driving load is large as the driver state, and
when the driver state detection unit detects that the driving load is large, the visual guidance unit emphasizes visual guidance, as compared with a case where the driver state detection unit detects that the driving load is small.

7. The visual perception assistance system according to claim 4, wherein
the driver state detection unit detects at least a state that the driver is absent-minded, as the driver state, and
when the driver state detection unit detects that the driver is absent-minded, the visual guidance unit emphasizes visual guidance, as compared with a case where the driver state detection unit detects that the driver is not absent-minded.

8. The visual perception assistance system according to claim 1, wherein
when a plurality of the overlooked visual perception targets are present, the visual guidance unit ranks the plurality of overlooked visual perception targets in a viewing order, and performs visual guidance of the plurality of overlooked visual perception targets by the ranking.

9. A visual perception target detection system, comprising:
a surrounding condition acquisition unit for acquiring a surrounding condition of an observer; and
a visual perception target determination unit for determining a visual perception target being an object that the observer should look at in a surrounding condition acquired by the surrounding condition acquisition unit, wherein
the visual perception target determination unit determines the visual perception target, based on three visual perception models prepared in advance, and
the three visual perception models include a saliency model for determining that an object to be visually perceived at a glance is a visual perception target, a surprise model for determining that an object behaving abnormally is a visual perception target, and a normative model for determining that an object to be visually perceived by a viewing action of an observer serving as a norm is a visual perception target.

10. The visual perception target detection system according to claim 9, further comprising:
a display unit for displaying a visual perception target determined by the visual perception target determination unit.

* * * * *